US00PP20352P2

(12) United States Plant Patent

De Jong

(10) Patent No.: US PP20,352 P2

(45) Date of Patent: Sep. 22, 2009

(54) *ASTRANTIA* PLANT NAMED 'STAR OF BILLION'

(50) Latin Name: ***Astrantia* hybrid**
Varietal Denomination: Star of Billion

(76) Inventor: Jacobus Robertus De Jong, Westerhout 89, Noordwijkerhout (NL), 2211 TN ( * ) Notice: Subject to any disclaimer, the term of this patent is extended or adjusted under 35 U.S.C. 154(b) by 0 days.

(21) Appl. No.: 12/150,372

(22) Filed: Apr. 28, 2008

(51) Int. Cl.
*A01H 5/00* (2006.01)

(52) U.S. Cl. ..... Plt./408

(58) Field of Classification Search ..... Plt./263, Plt./408

See application file for complete search history.

*Primary Examiner*—Susan B McCormick Ewoldt

(74) *Attorney, Agent, or Firm*—Jondle & Associates, P.C.

(57) ABSTRACT

A new *Astrantia* plant particularly distinguished by its white flowers and white bracts with green tips, large inflorescences with very rich flowering and strong color, strong growth and high durability of foliage to stress, is disclosed.

2 Drawing Sheets

Genus and species: *Astrantia* hybrid.
Variety denomination: 'Star of Billion'.

BACKGROUND OF THE NEW PLANT

The present invention comprises a new and distinct cultivar of *Astrantia,* botanically known as *Astrantia* and hereinafter referred to by the cultivar name 'Star of Billion'. The new cultivar originated from an open pollination made in 2001 in Woubrugge, The Netherlands between the female parent, an unnamed selection of *Astrantia major* (unpatented), and the male parent, an unknown and unnamed selection of *Astrantia* (unpatented). The seeds produced by the open pollination were sown and a single plant selection was chosen for further evaluation and for asexual propagation in 2004 in Woubrugge, The Netherlands.

The new cultivar was created in 2001 in Woubrugge, The Netherlands and has been asexually reproduced repeatedly by division and tissue culture in Woubrugge and De Hoef, The Netherlands, over a three-year period. The present invention has been found to retain its distinctive characteristics through successive asexual propagations.

Plant Breeder's Rights for this cultivar were applied for in the European Union on Oct. 11, 2007. 'Star of Billion' has not been made publicly available more than one year prior to filing of this application.

SUMMARY OF THE INVENTION

The following are the most outstanding and distinguishing characteristics of this new cultivar when grown under normal horticultural practices in Woubrugge, The Netherlands:

1. White flowers and white bracts with green tips;
2. Large inflorescences with very rich flowering and strong color;
3. Strong growth; and
4. High durability of foliage to stress.

DESCRIPTION OF THE PHOTOGRAPHS

This new *Astrantia* plant is illustrated by the accompanying photographs which show blooms, buds, and foliage of the plant in full color; the colors shown are as true as can be reasonably obtained by conventional photographic procedures. The photographs are of plants that are two-years-old and grown in a field with natural light.

DESCRIPTION OF THE NEW CULTIVAR

Figure 1:
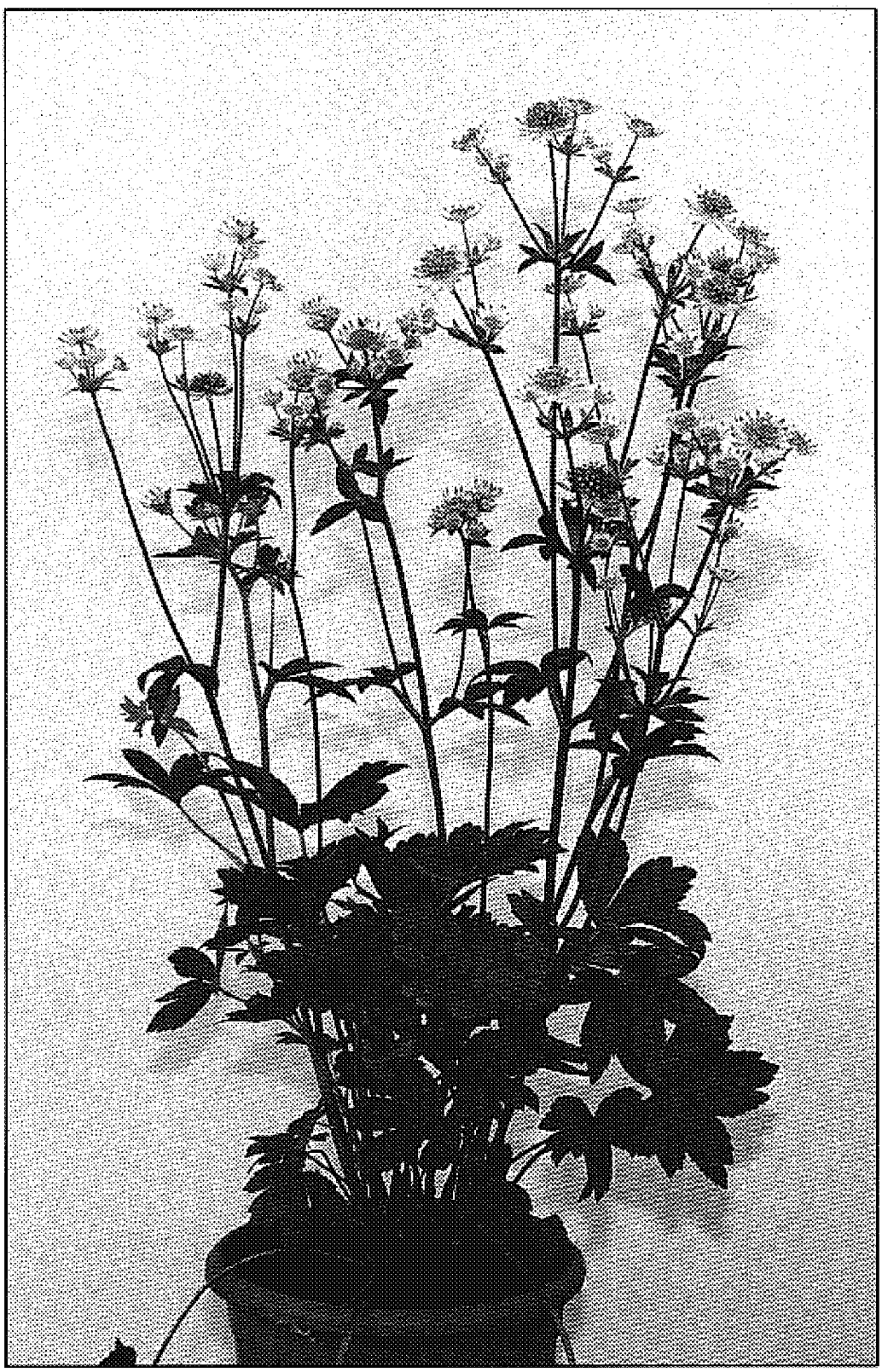
FIG. 1 shows the overall plant habit including blooms, buds, and mature foliage.
Figure 2:
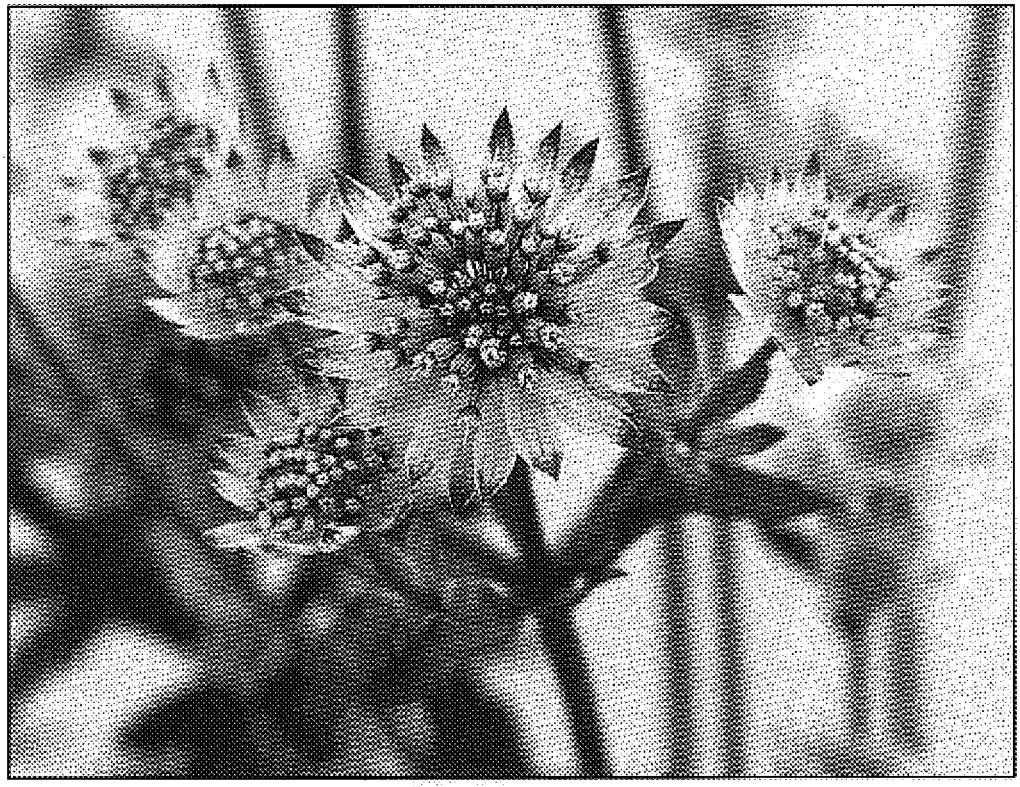
FIG. 2 shows a close-up of the mature flowers.
Figure 3:
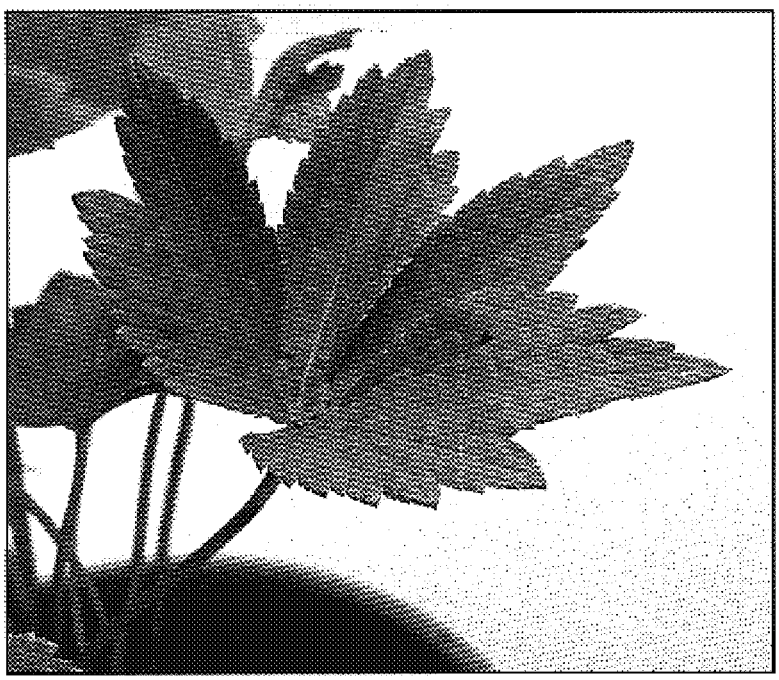
FIG. 3 shows a close-up a leaf.

The following detailed descriptions set forth the distinctive characteristics of 'Star of Billion'. The data which define these characteristics were collected from asexual reproductions carried out in De Hoef, The Netherlands. The plant history was taken on two-year-old plants grown from rooted cuttings in a field under normal outdoor light. Daytime temperatures ranged from 14° C. at 30° C. and night time temperatures ranged from 4° C. to 16° C. Plants were not pinched nor were growth retardants used. Color readings were taken under natural light. Color references are primarily to the R.H.S. Colour Chart of The Royal Horticultural Society of London (R.H.S.) (2001 edition).

DESCRIPTION OF THE NEW PLANT

Classification:
- *Family.*—Apiaceae.
- *Botanical name.*—*Astrantia* hybrid.
- *Common.*—Great masterwort.

Parentage:
- *Female parent.*—An unnamed selection of *Astrantia major* (unpatented).
- *Male parent.*—An unknown and unnamed selection of *Astrantia* (unpatented).

Plant:
- *Type.*—Herbaceous perennial.
- *Plant shape.*—Globular with flowering stems on the top.
- *Plant habit.*—Basal rosette with flowering stems growing from the base.
- *Vigor.*—Moderate; growth is about 15 cm per month.

*Height.*—64.6 cm.
*Diameter (spread).*—48.6 cm.
*Time to produce a finished flowering plant.*—About 19 weeks.
*Appropriate container systems.*—Use in pots or flowering beds.
*Garden performance.*—Highly tolerant to rain and wind; tolerant to high temperature of 30° C. and hardy to at least USDA Zone 6.

Branches:
*Branching.*—Basal branching; stems grow moderately free from a basal rosette.
*Number of flowering branches.*—6.
*Length of flowering branch.*—22.3 cm from the base to the lowest branching inflorescence.
*Diameter of flowering branch.*—0.5 cm.
*Internode length.*—13.8 cm.
*Appearance/shape.*—Rounded, ribbed lengthwise, slightly glossy.
*Aspect.*—Slightly ribbed lengthwise.
*Strength.*—Strong.
*Color.*—RHS 144A (yellow-green).
*Pubescence.*—Absent.

Leaves:
*Arrangement.*—Alternate, single.
*Quantity per branch.*—About 2; the whole plant has an average of 42 leaves, 30 of which are in the basal rosette.
*Shape.*—Palmately parted.
*Apex.*—Acute.
*Base.*—Hastate, the lower lobes are not overlapping.
*Margin.*—Biserrate; average of 3 large teeth per 2 cm of margin; average of 4 smaller teeth per large tooth; the teeth are aristate.
*Pubescence.*—Absent.
*Color, immature leaf.*—Upper surface: Between RHS 143A and RHS 144A (yellow-green). Lower surface: RHS 143C (green).
*Color, mature leaf.*—Upper surface: RHS 137A (green). Lower surface: Between RHS 137C and RHS 147B (yellow-green).
*Length.*—Basal leaf: 9.1 cm. Stem leaf: 6.9 cm.
*Width.*—Basal leaf: 12.4 cm. Stem leaf: 9.5 cm.
*Texture.*—Smooth.
*Venation pattern.*—Laciniate.
*Vein color.*—Upper: RHS 143A to RHS 143B (yellow-green). Lower: RHS 144A to RHS 144B (yellow-green).
*Petiole.*—Basal leaf: Length: 20.5 cm. Diameter: 0.2 cm. Shape: Ovate. Height: 0.3 cm. Color: RHS 144A and the base is lighter, RHS 144B. Stem leaf: General: Stem leaf is sheathed. Length: 6.4 cm. Height: 0.4 cm. Diameter: 0.8 cm. Color: Between RHS 143B and RHS 144A (yellow-green). Durability of foliage to stresses: High.

Flower bud:
*Length.*—0.6 cm.
*Diameter.*—0.2 cm.
*Shape.*—Obovate with a flattened top.
*Color.*—RHS 65A (red-purple) and the base is RHS 144A (yellow-green).

Inflorescence:
*Shape/arrangement.*—Compound umbel.
*Height (including the peduncle).*—39.7 cm.
*Width.*—15.3 cm.
*Quantity of flowers per inflorescence.*—60 flowers per umbel; about 30 umbels per compound umbel.
*Flowering habit.*—Once per year, late spring into summer but continuous during that time.
*Quantity of flowers per flowering stem.*—1,800.
*Quantity of flower buds per flowering stem.*—1,800.
*Quantity of flowers and buds per plant.*—10,000.
*Time to produce flowers on the plant.*—Approximately 9 months (for field-grown plants).
*Rate of flower opening.*—Approximately 5% of flowers are open at once (central umbels) followed by secondary umbels.
*Fragrance.*—Very faint and relatively unpleasant.

Flowers:
*Aspect.*—Upright and upright-outward.
*Shape.*—Rotate.
*Diameter.*—0.25 cm.
*Height (depth).*—1.0 cm.
*Lastingness of flowers on the plant.*—12 days.
*Persistent or self-cleaning.*—Self-cleaning.

Petals:
*Quantity (per flower).*—5.
*Arrangement.*—Rotate and upright; petals are not fused.
*Surface.*—Dull and smooth.
*Size.*—Length: 0.2 cm. Width: 0.1 cm.
*Shape.*—Ovate, recurved.
*Apex.*—Narrow acute.
*Margin.*—Entire.
*Color, when opening (both surfaces).*—RHS 69C and RHS 69D (red-purple) to RHS N155B and RHS N155C (white).
*Color, when fully opened (both surfaces).*—RHS N155B and RHS N155C (white).

Calyx:
*Shape.*—Rotate, the sepals are upright.
*Length.*—0.15 cm.
*Diameter.*—0.2 cm.

Sepals:
*Arrangement.*—Rotate and upright.
*Quantity.*—5 sepals.
*Texture (both surfaces).*—Dull, smooth.
*Shape.*—Ovate.
*Apex.*—Broad acute.
*Base.*—Cuneate.
*Margin.*—Entire.
*Color, immature (both surfaces).*—RHS 65A (red-purple) and base is RHS 144A (yellow-green).
*Color, mature (both surfaces).*—RHS 69C and RHS 69D (red-purple), margins are RHS 65A (darker red-purple) and the base is RHS 144A (yellow-green).
*Length.*—0.15 cm.
*Width.*—0.08 cm.

Bracts:
*General.*—A ring of bracts is placed under each umbel.
*Number.*—20.
*Shape.*—Elliptic.
*Apex.*—Acute.
*Base.*—Attenuate.
*Margin.*—Entire.
*Length.*—1.6 cm.
*Width.*—0.355 cm.
*Texture.*—Dull and smooth.
*Color (both surfaces).*—RHS 157C to RHS 157D with RHS 143A tips.

Pedicel:

*Length.*—0.4 cm.

*Diameter.*—0.03 cm.

*Angle.*—Central flowers straight upright; outer flowers 80°.

*Color.*—RHS 65A (red-purple).

*Strength.*—Strong.

Peduncle:

*Length.*—4.0 cm.

*Diameter.*—0.2 cm.

*Angle.*—Primary umbel straight upright; secondary umbels average angle of 30°.

*Color.*—RHS 143A to RHS 143B (yellow-green).

*Strength.*—Strong.

Reproductive organs:

*Stamens.*—None.

*Pistil.*—Pistil number: 2. Pistil length: 0.2 cm. Stigma shape: Club-shaped. Stigma color: RHS N155B (white). Style length: 0.18 cm. Style color: RHS N155B (white). Ovary color: RHS 193A to RHS 193B (greyed-green).

Fruit and seed set: None.

Disease and insect resistance: No susceptibility to common diseases or pests has been observed.

COMPARISON WITH PARENTAL AND COMMERCIAL CULTIVARS

'Star of Billion' differs from the female parent, an unnamed and unpatented selection of *Astrantia major,* in that 'Star of Billion' has many more flowers and larger inflorescences than the female parent.

'Star of Billion' differs from the commercial *Astrantia* variety 'Venice' (U.S. Plant Pat. No. 18,420) in that 'Star of Billion' has an average plant diameter of 48.6 cm while 'Venice' has an average plant diameter of 33 cm. In addition, 'Star of Billion' has an average of 6 flowering branches, 60 flowers per umbel and a fully opened petal color of RHS N155B to RHS N155C while 'Venice ' has an average of 3 branches, 80 flowers per umbel and a fully opened petal color of between RHS 59C and RHS 60B.

I claim:

1. A new and distinct cultivar of *Astrantia* plant as shown and described herein.

* * * * *